United States Patent
Wolf

[11] Patent Number: 5,817,147
[45] Date of Patent: Oct. 6, 1998

[54] HYPOTHERMIC ENVELOPE AND APPARATUS FOR PROVIDING COOLED AIR THERETO

[76] Inventor: Suzanne M. Wolf, Rd. #1 Box 133, Eldred, Pa. 16731

[21] Appl. No.: 870,036

[22] Filed: Jun. 5, 1997

[51] Int. Cl.⁶ ........................................................ A61F 7/00
[52] U.S. Cl. ...................... 607/104; 607/107; 126/204; 5/423; 62/209.3
[58] Field of Search ................................. 607/104, 107, 607/108, 114; 126/204; 5/423; 62/259.3; 165/46

[56] References Cited

U.S. PATENT DOCUMENTS

| | | | |
|---|---|---|---|
| 3,714,947 | 2/1973 | Hardy | 607/104 |
| 5,383,918 | 1/1995 | Panetta | 607/104 |
| 5,405,370 | 4/1995 | Irani | 607/104 |
| 5,443,488 | 8/1995 | Nameneye et al. | 607/107 |
| 5,545,196 | 8/1996 | Falk | 607/107 |
| 5,674,269 | 10/1997 | Augustine | 607/107 |

Primary Examiner—Robert L. Nasser

[57] ABSTRACT

A new Hypothermic Envelope and Apparatus for Providing Cooled Air Thereto for the emergency medical treatment of accident and other trauma victims whereby the victim's body temperature is lowered to induce a state of controlled hypothermia in order to slow the victim's body metabolism and thereby decrease the adverse effects of the victim's injuries. The inventive device includes coextensive top and bottom portion, the top portion and the bottom portion being sealingly connectable at their peripheries and forming an envelope therebetween and a microcontroller operably connected to a fan motor for producing a burst of cool air by means of passing air over a refrigerant's cooling coil and thereby providing a controlled amount of cool air to the envelope.

20 Claims, 6 Drawing Sheets

HYPOTHERMIC ENVELOPE AND APPARATUS FOR PROVIDING COOLED AIR THERETO

BACKGROUND OF THE INVENTION

1. Field of the Invention

The present invention relates to patient warming and cooling devices and more particularly pertains to a new Hypothermic Envelope and Apparatus for Providing Cooled Air Thereto for the emergency medical treatment of accident and other trauma victims whereby the victim's body temperature is lowered to induce a state of controlled hypothermia in order to slow the victim's body metabolism and thereby decrease the adverse effects of the victim's injuries.

2. Description of the Prior Art

The use of patient warming and cooling devices is known in the prior art. More specifically, patient warming and cooling devices heretofore devised and utilized are known to consist basically of familiar, expected and obvious structural configurations, notwithstanding the myriad of designs encompassed by the crowded prior art which have been developed for the fulfillment of countless objectives and requirements.

Known prior art patient warming and cooling devices include U.S. Pat. No. 5,304,213; U.S. Pat. No. 5,125,392; U.S. Pat. No. 5,318,568; U.S. Pat. No. 4,777,802; and U.S. Pat. No. 5,300,100.

While these devices fulfill their respective, particular objectives and requirements, the aforementioned patents do not disclose a new Hypothermic Envelope and Apparatus for Providing Cooled Air Thereto. The inventive device includes coextensive top and bottom portion, the top portion and the bottom portion being sealingly connectable at their peripheries and forming an envelope therebetween and a means for providing a controlled amount of cool air to the envelope.

In these respects, the Hypothermic Envelope and Apparatus for Providing Cooled Air Thereto according to the present invention substantially departs from the conventional concepts and designs of the prior art, and in so doing provides an apparatus primarily developed for the purpose of the emergency medical treatment of accident and other trauma victims whereby the victim's body temperature is lowered to induce a state of controlled hypothermia in order to slow the victim's body metabolism and thereby decrease the adverse effects of the victim's injuries.

SUMMARY OF THE INVENTION

In view of the foregoing disadvantages inherent in the known types of patient warming and cooling devices now present in the prior art, the present invention provides a new Hypothermic Envelope and Apparatus for Providing Cooled Air Thereto construction wherein the same can be utilized for the emergency medical treatment of accident and other trauma victims whereby the victim's body temperature is lowered to induce a state of controlled hypothermia in order to slow the victim's body metabolism and thereby decrease the adverse effects of the victim's injuries.

The general purpose of the present invention, which will be described subsequently in greater detail, is to provide a new Hypothermic Envelope and Apparatus for Providing Cooled Air Thereto apparatus and method which has many of the advantages of the patient warming and cooling devices mentioned heretofore and many novel features that result in a new Hypothermic Envelope and Apparatus for Providing Cooled Air Thereto which is not anticipated, rendered obvious, suggested, or even implied by any of the prior art patient warming and cooling devices, either alone or in any combination thereof.

To attain this, the present invention generally comprises coextensive top and bottom portion, the top portion and the bottom portion being sealingly connectable at their peripheries and forming an envelope therebetween and a means for providing a controlled amount of cool air to the envelope.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new Hypothermic Envelope and Apparatus for Providing Cooled Air Thereto apparatus and method which has many of the advantages of the patient warming and cooling devices mentioned heretofore and many novel features that result in a new Hypothermic Envelope and Apparatus for Providing Cooled Air Thereto which is not anticipated, rendered obvious, suggested, or even implied by any of the prior art patient warming and cooling devices, either alone or in any combination thereof.

It is another object of the present invention to provide a new Hypothermic Envelope and Apparatus for Providing Cooled Air Thereto which may be easily and efficiently manufactured and marketed.

It is a further object of the present invention to provide a new Hypothermic Envelope and Apparatus for Providing Cooled Air Thereto which is of a durable and reliable construction.

An even further object of the present invention is to provide a new Hypothermic Envelope and Apparatus for Providing Cooled Air Thereto which is susceptible of a low cost of manufacture with regard to both materials and labor, and which accordingly is then susceptible of low prices of sale to the consuming public, thereby making such Hypothermic Envelope and Apparatus for Providing Cooled Air Thereto economically available to the buying public.

Still yet another object of the present invention is to provide a new Hypothermic Envelope and Apparatus for Providing Cooled Air Thereto which provides in the apparatuses and methods of the prior art some of the advantages thereof, while simultaneously overcoming some of the disadvantages normally associated therewith.

Still another object of the present invention is to provide a new Hypothermic Envelope and Apparatus for Providing Cooled Air Thereto for the emergency medical treatment of accident and other trauma victims whereby the victim's body temperature is lowered to induce a state of controlled hypothermia in order to slow the victim's body metabolism and thereby decrease the adverse effects of the victim's injuries.

Yet another object of the present invention is to provide a new Hypothermic Envelope and Apparatus for Providing Cooled Air Thereto which includes coextensive top and bottom portion, the top portion and the bottom portion being sealingly connectable at their peripheries and forming an envelope therebetween and a means for providing a controlled amount of cool air to the envelope.

Still yet another object of the present invention is to provide a new Hypothermic Envelope and Apparatus for Providing Cooled Air Thereto that easily cleaned.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

With reference now to the drawings, and in particular to FIGS. 1 through 9 thereof, a new Hypothermic Envelope and Apparatus for Providing Cooled Air Thereto embodying the principles and concepts of the present invention and generally designated by the reference numeral 10 will be described.

More specifically, it will be noted that the Hypothermic Envelope and Apparatus for Providing Cooled Air Thereto 10 comprises coextensive top and bottom portions 13 and 14 respectively, the top portion 13 and the bottom portion 14 being sealingly connectable at their peripheries and forming an envelope 12 therebetween and a means for providing a controlled amount of cool air 40 to the envelope 12.

Figures 1, 2:
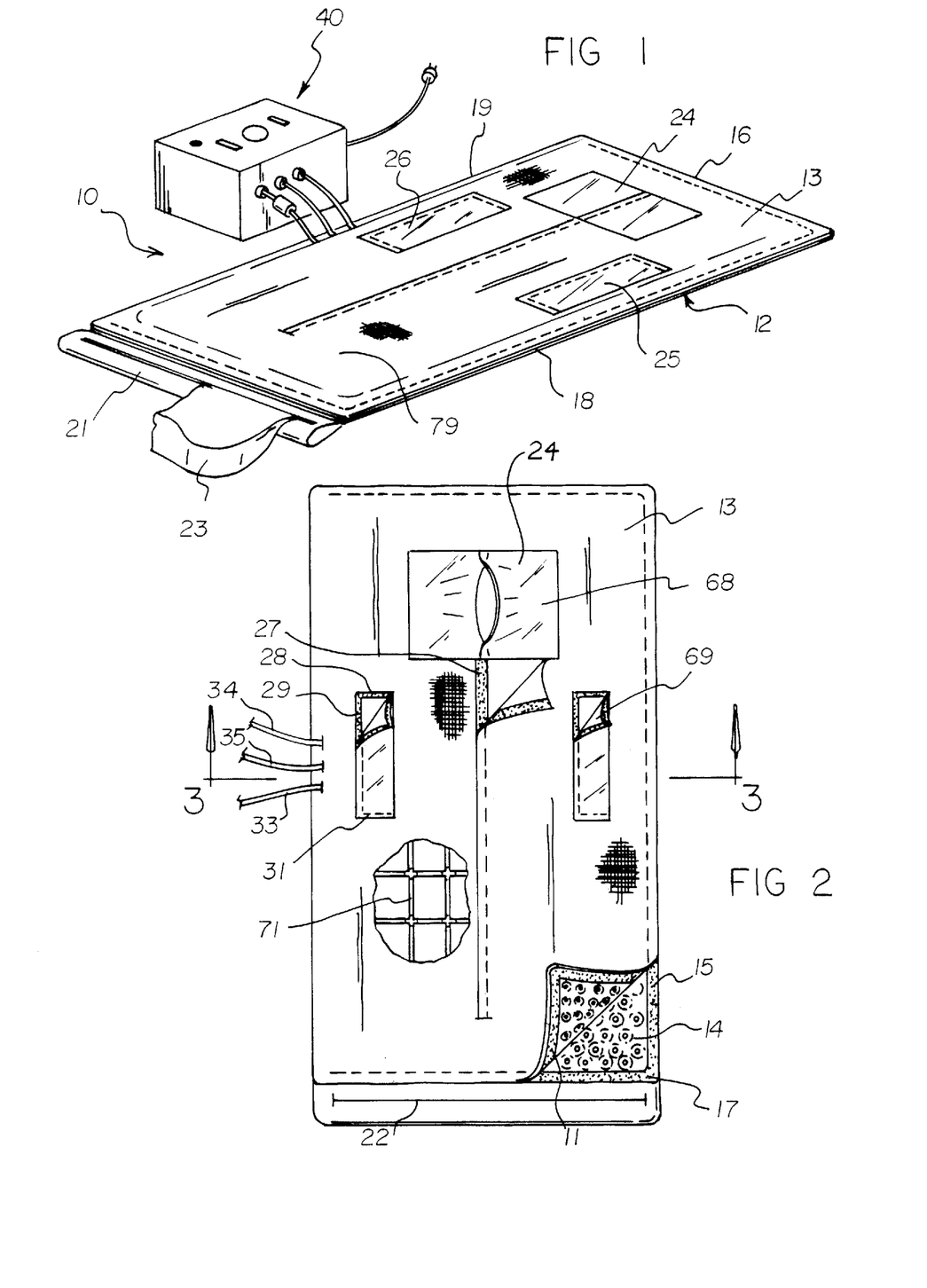
FIG. 1 is a right side perspective view of a new Hypothermic Envelope and Apparatus for Providing Cooled Air Thereto according to the present invention.
FIG. 2 is a top plan view thereof.

With reference to FIG. 1 the envelope 12 is shown including a top edge 16, a bottom edge having a pouch 21 attached thereto, a first lateral edge 18 and a second lateral edge 19. The top edge 16, bottom edge and first lateral edge 18 are formed from joining the respective and coextensive edges of the top portion 13 and bottom portion 14 as with a hook and eye fastening system 15 such as Velcro™ (FIG. 2).

With continued reference to FIG. 1 there is shown a head area aperture 24, a first arm and hand aperture 25 and a second arm and hand aperture 26 formed in the top portion 13. The head area aperture 24 allows access to the trauma victim's head and neck when the trauma victim is within the envelope 12. The first and second arm and hand apertures 25 and 26 allow access to the trauma victim's arms and hands when the trauma victim is within the envelope.

A means for extending the length of the envelope 12 is shown including an enclosure 23 disposed within the pouch 21. The pouch 21 is shown fixedly attached to a bottom portion bottom edge 17 (FIG. 2). The enclosure 23 has a first edge (not shown) fixedly attached to the bottom portion bottom edge 17 and a second edge (not shown) removably attachable to a top portion bottom edge 11. A closable opening 22 is shown and in the preferred embodiment is closable by means of a zipper.

With continued reference to FIG. 2 the head area aperture 24 is shown having a pair of overlapping windows 68. The overlapping windows 68 are formed of a clear self-adhering plastic material and each overlapping window 68 is shown fixedly attached to a head area aperture perimeter at each of three overlapping window peripheral edges and each fourth peripheral edge being disposed in overlapping relationship with the other.

A sealingly fastenable opening 27 is shown extending from the head area aperture 24 and terminating at a top portion foot section 79 for allowing quick access to the trauma victim. Also shown are means for sealingly covering the first and second arm and hand apertures 25 and 26. A flap 69 is formed from the top portion 13 and is sealingly attachable at an arm and hand aperture top edge 28, an arm and hand aperture lateral edge 29 and an arm and hand aperture bottom edge 31.

With continued reference to FIG. 2 there is shown a return network of tubing 71 disposed in the top portion 13. An air inlet line 34 and an electrical cable 35 are shown entering the envelope 12. An air return line 33 is shown exiting the envelope 12. The purpose and function of the return network of tubing 71, the air inlet line 34, the electrical cable 35 and the air return line 33 will be more fully described hereinafter.

Figure 3:
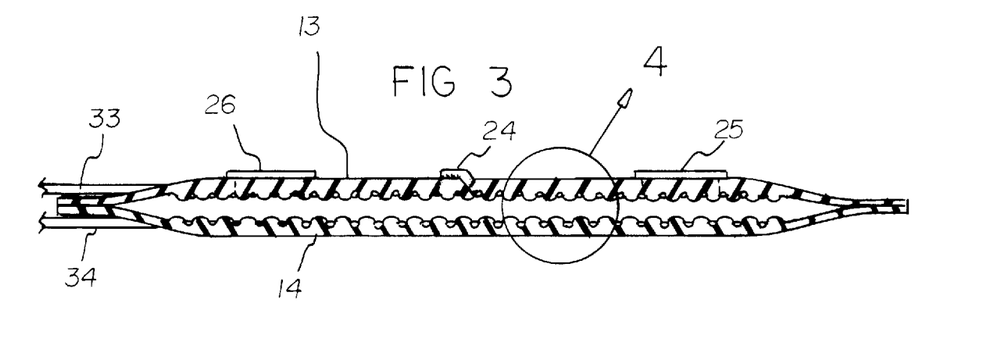
FIG. 3 is cross sectional view of the present invention taken along line 3—3 of FIG. 2.
Figure 4:
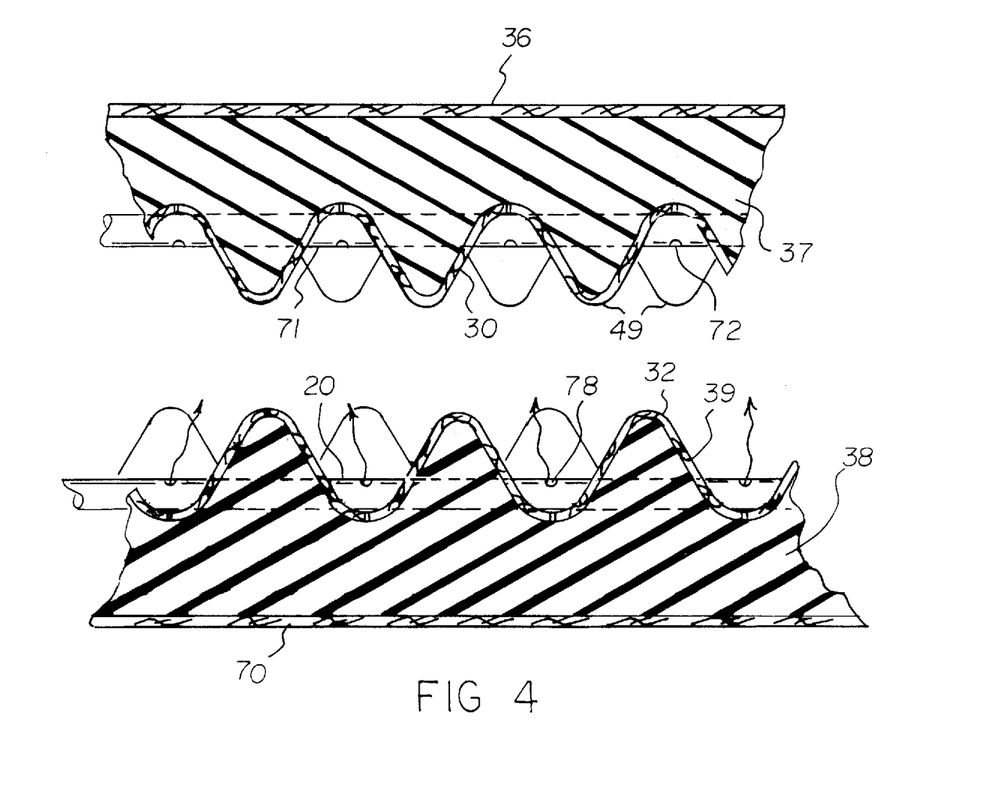
FIG. 4 is a fragmented and enlarged view showing the construction of the upper and lower layers of the invention.

With reference to FIG. 3 there is shown in greater detail the top portion 13 and bottom portion 14. With reference to FIG. 4 top portion 13 includes a top portion top layer 36, a top portion middle layer 37 and a top portion bottom layer 30. The bottom portion 14 includes a bottom portion top layer 39, a bottom portion middle layer 38 and a bottom portion bottom layer 70. The top portion top layer 36 and the bottom portion bottom layer 70 are of nylon construction. The top layer middle layer 37 and the bottom portion middle layer 38 are constructed of foam with the bottom portion middle layer being of greater thickness and adapted to support the weight of the trauma victim. The top portion bottom layer 30 and the bottom portion top layer 39 are constructed of aluminumized polyethylene for ease of cleaning of the envelope 12.

With continued reference to FIG. 4 there is shown an air supply network 20 consisting of a rectangular network of polyvinylchloride tubing having a plurality of supply apertures 78 formed at one half inch intervals along the air supply network 20. The air supply network 20 is shown fixedly attached in a plane formed at the bases of a plurality of conical bottom portion protrusions 32. In similar fashion an air return network 71 consisting of a rectangular network of polyvinylchloride tubing having a plurality of return apertures 72 formed at one half inch intervals along the air return network 71 is shown fixedly attached in a plane formed at the bases of a plurality of conical top portion protrusions 49. In this manner the trauma victim does not lay upon the air supply network 20 and cool air flows around the trauma victim as more fully described hereinafter. Additionally, the air return network 71 does not contact the trauma victim and air is allowed to return to the cooling apparatus 40.

Figure 6:
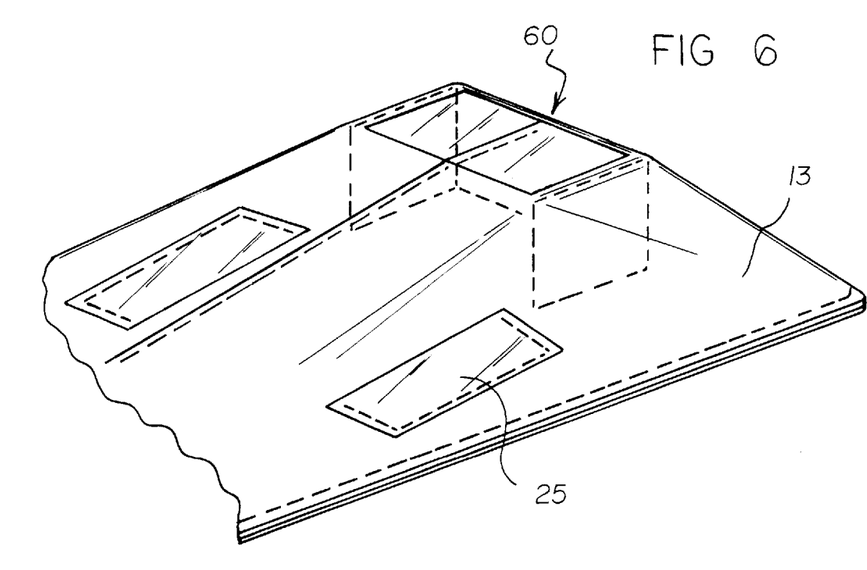
FIG. 6 is fragmented view of the hypothermic envelope showing the positioning of the head area support apparatus of the present invention.
Figure 7:
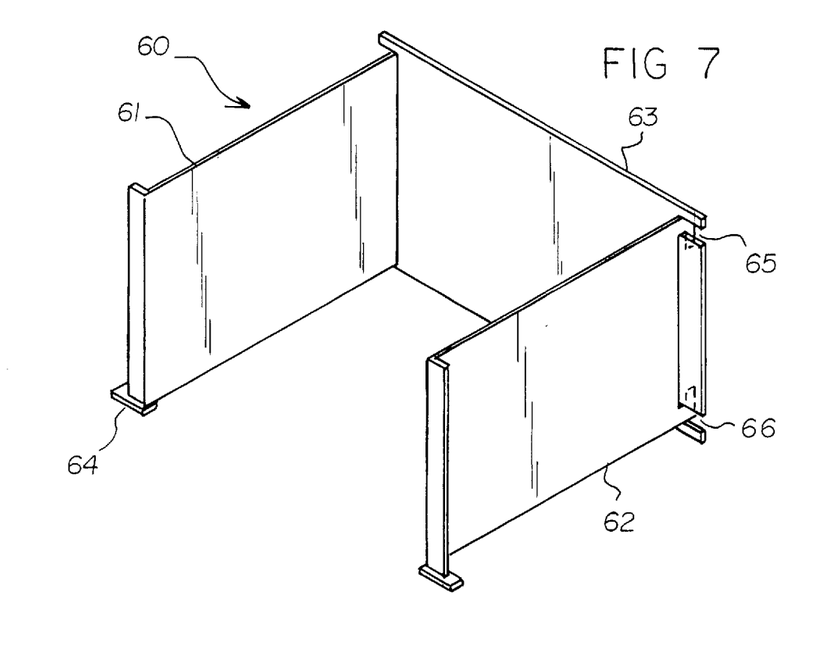
FIG. 7 is a perspective view of the head support apparatus.

With reference to FIG. 6 there is shown the head area support apparatus 60 disposed within the envelope 12. As more clearly shown in FIG. 7, the head area support apparatus 60 consists of a first and second lateral spline 61 and 62 and a back spline 63. The first and second lateral splines 61 and 62 and the back spline 63 are interlockingly disengagable by means of slots 66 and engaging members 65 formed thereon. Also shown are a pair of support members 64 for providing added support to the head area support apparatus 60. In use the head area support apparatus 60 prevents the top portion 13 from exerting pressure upon the trauma victim's head.

Figure 5:
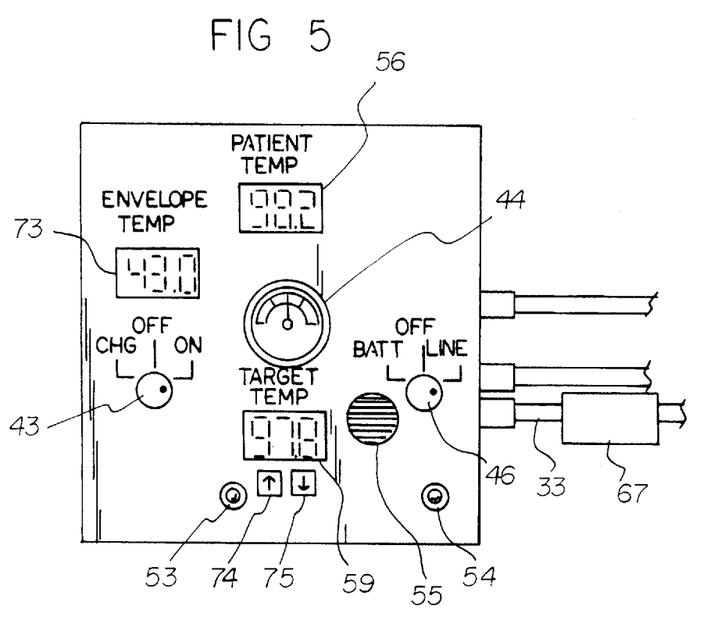
FIG. 5 is a plan view of the external air supply unit of the present invention.

With reference to FIG. 5 there is shown the front panel of the cooling apparatus 40. The trauma victim's temperature is displayed as the patient temperature 56. A target temperature display 59 is shown as well as means for increasing and decreasing the target temperature 74 and 75. An envelope temperature display 73 is also shown.

With continued reference to FIG. 5 a switch 43 allows for turning on and off the cooling apparatus 40 and also for charging a battery 41. A power select switch 46 is provided and allows for selection of a power source for the cooling apparatus 40 and alternatively allows for turning the cooling apparatus 40 off. A temperature alarm switch 53 is also shown. A buzzer grill is shown behind which is disposed an audible alarm 55. A voltmeter 44 is also shown together with a temperature alarm light 54.

With continued reference to FIG. 5 there is shown a condenser 67 connected to the return line 33. The condenser is adapted to remove moisture from the air returning to the cooling apparatus through the return line 33.

Figure 8:
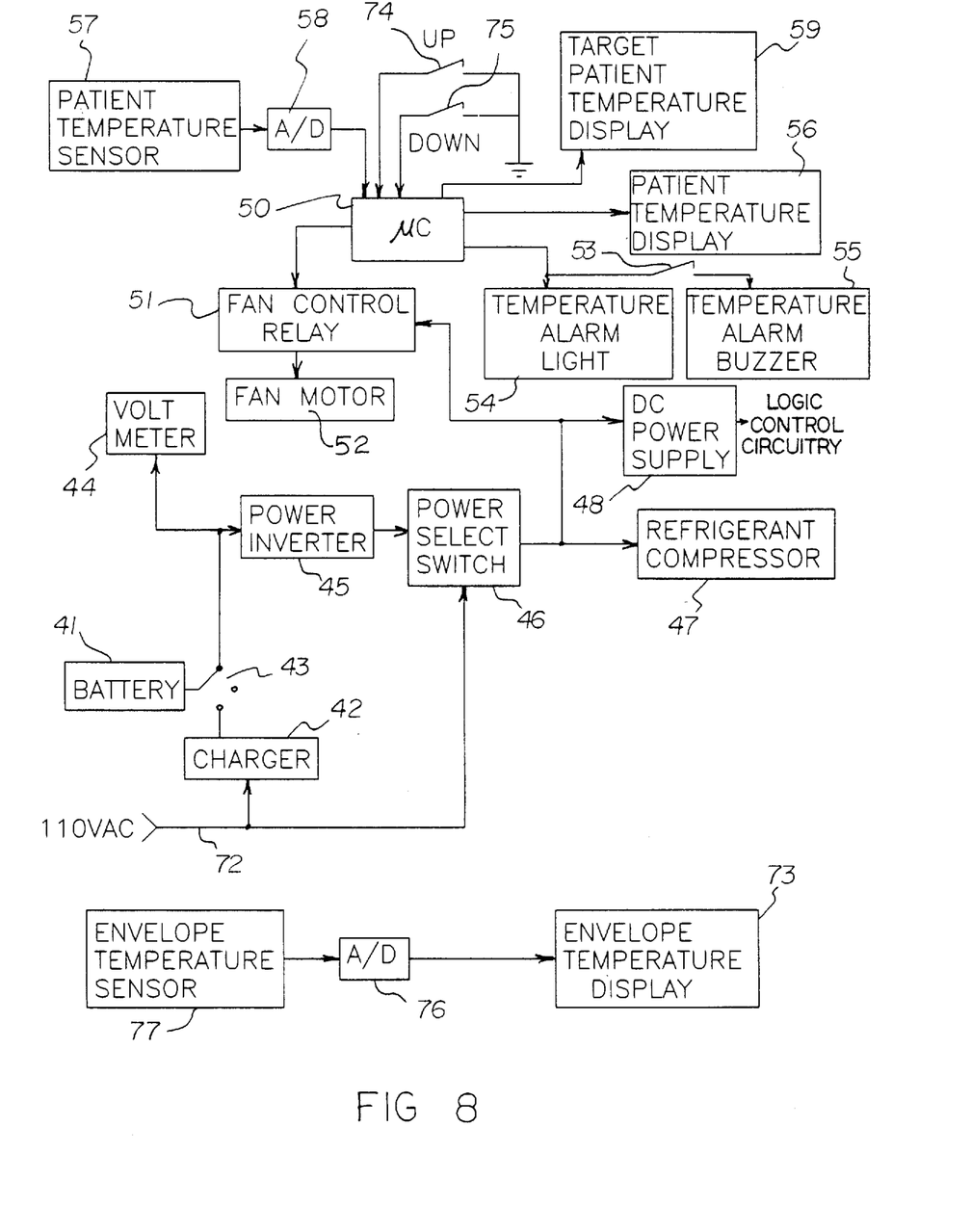
FIG. 8 is a schematic block diagram showing the control circuitry of the present invention.

With reference to FIG. 8 a programmable microcontroller 50 is shown operably connected to a patient temperature sensor 57 through an analog to digital converter 58. The patient temperature sensor 57 is disposed either rectally or esophageally in the patient. A means for increasing or decreasing a target patient temperature including an up momentary switch 74 and a down momentary switch 75 is also shown operably connected to the microcontroller 50. The patient temperature display 56 as well as the target patient temperature display 59 are shown operably connected to the microcontroller 50.

With continued reference to FIG. 8 a fan control relay 51 is shown operably connected to the microcontroller 50. The fan control relay 51 is under the control of the microcontroller 50 and operates to power a fan motor which forces air over the cooling coil of a refrigerant compressor 47 and into the air supply network. Also shown operably connected to the microcontroller 50 is the temperature alarm light 54 as well as the temperature alarm buzzer 55. The switch 53 is operable to disconnect the temperature alarm buzzer 55 from the circuit.

The circuit is powered by either a line voltage or a battery 41. A power select switch 46 is shown for this purpose. A battery charger 42 is provided for charging the battery 41 which is shown operably connected to a power inverter 45 for powering the refrigerant compressor 47. A voltmeter 44 is shown for displaying the battery voltage. A DC power supply is operably connected to either power source (line or battery) for providing DC voltage to the logic control circuitry (microcontroller 50 and associated displays, sensors and alarm circuits). The fan control relay 51 and fan motor 52 are also shown operably connected to the power select switch 46.

An envelope temperature sensor 77 is shown. The envelope temperature sensor 77 is disposed within the envelope 12 and is shown connected to an analog to digital converter 76. The analog to digital converter 76 is in turn operably connected to an envelope temperature display 73.

Figure 9:
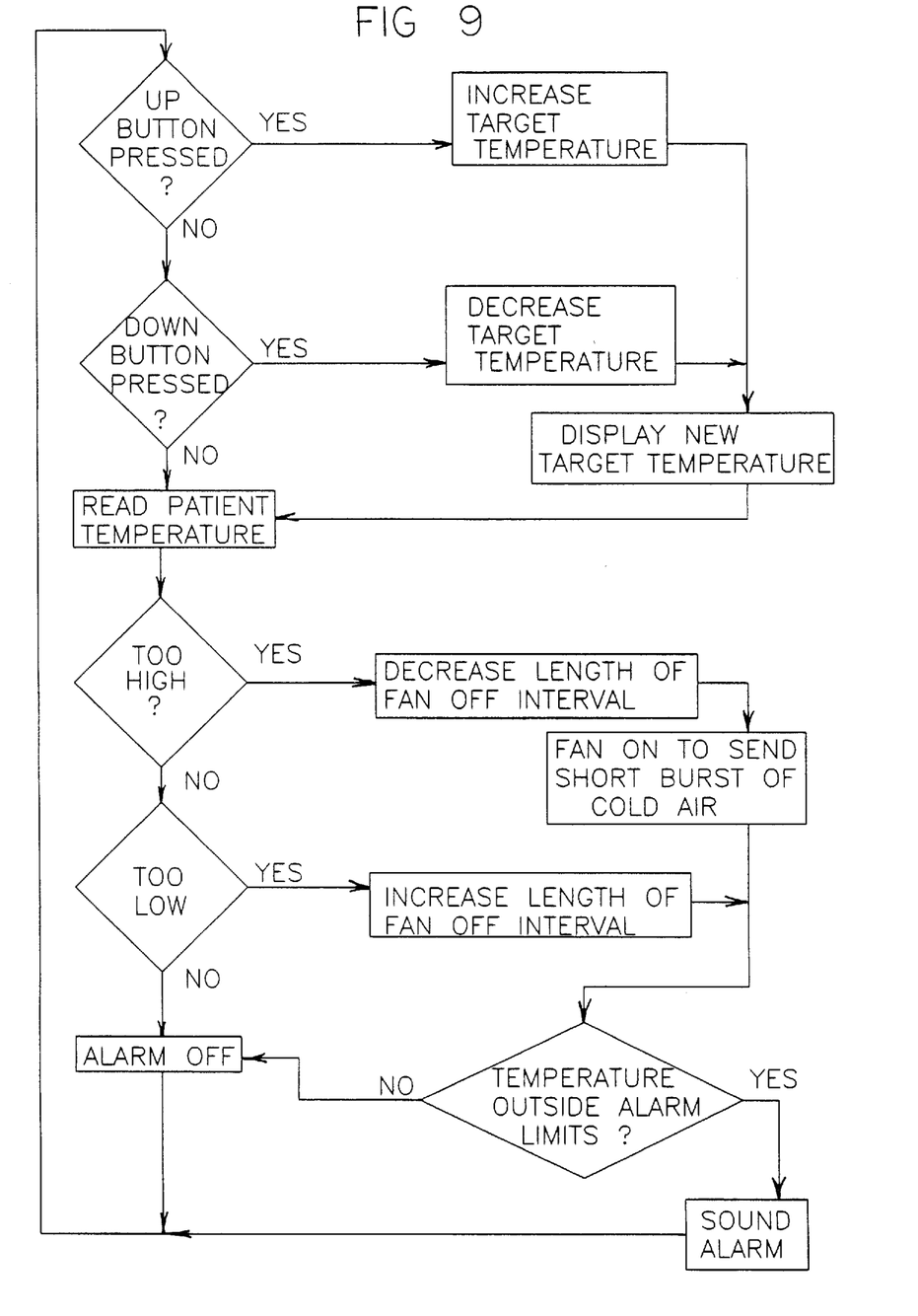
FIG. 9 is a flow diagram illustrating the programming of the microcontroller as it is used to control the inside temperature of the envelope.

In use, a trauma victim is placed within the envelope 12 and the temperature sensor is placed in the patient. A target temperature is selected by means of the up switch 74 or the down switch 75 and the target temperature is displayed on the target patient temperature display 59. The microcontroller 50 then compares the target temperature with the patient's temperature. If the patient's temperature is above the target temperature then the length of time the fan is off is decreased and the fan motor is turned on to send a short burst of air over the cooling coil and through the air supply network. If, on the other hand, the patient's temperature is below the target temperature then the length of time the fan if off is increased. If the patient's temperature is outside of a preprogrammed alarm limit then the temperature alarm light 54 is activated as well as the temperature alarm buzzer 55.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A hypothermic envelope and apparatus for providing cooled air thereto for use with a trauma victim comprising:

coextensive top and bottom portions, the top portion and the bottom portion being sealingly connectable at their peripheries and forming an envelope therebetween;

a means for providing a controlled amount of cool air to the envelope;

wherein the top portion further comprises a means for sealingly covering a head area aperture, the head area aperture being formed in the top portion and disposed in such a manner as to allow for viewing and access to the trauma victim's head and neck when the trauma victim is within the envelope; and wherein the means for sealingly covering the head area aperture further comprises a pair of overlapping windows formed of a clear self-adhering plastic material, each overlapping window being fixedly attached to a head area aperture perimeter at each of three overlapping window peripheral edges and each fourth peripheral edge being disposed in overlapping relationship with the other.

2. The hypothermic envelope and apparatus for providing cooled air thereto of claim 1, wherein the top portion further comprises a sealingly fastenable opening disposed along a longitudinal axis of the top portion, the sealingly fastenable opening extending from the head area aperture to a top portion foot section.

3. The hypothermic envelope and apparatus for providing cooled air thereto of claim 1, wherein the means for providing a controlled amount of cool air to the envelope further comprise a control means for energizing a fan in response to a positive difference between a trauma victim's temperature and a target temperature.

4. The hypothermic envelope and apparatus for providing cooled air thereto of claim 2, wherein the means for providing a controlled amount of cool air to the envelope further comprise a refrigerant compressor having a cooling coil and wherein the fan blows a controlled amount of air over the cooling coil and into a supply network of tubing.

5. A hypothermic envelope and apparatus for providing cooled air thereto for use with a trauma victim comprising:

coextensive top and bottom portions, the top portion and the bottom portion being sealingly connectable at their peripheries and forming an envelope therebetween;

a means for providing a controlled amount of cool air to the envelope;

wherein the top portion further comprises a means for sealingly covering a pair of arm and hand area apertures, the arm and hand area apertures being formed in the top portion and disposed in such a manner as to allow for access to each of the trauma victim's arm and hand when the trauma victim in within the envelope; and wherein the means for sealingly covering each arm and hand area aperture further comprises a flap formed from the top portion, the flap being sealingly fastenable by means of a hook and eye fastening system.

6. The hypothermic envelope and apparatus for providing cooled air thereto of claim 5, wherein the means for providing a controlled amount of cool air to the envelope further comprise a control means for energizing a fan in response to a positive difference between a trauma victim's temperature and a target temperature.

7. The hypothermic envelope and apparatus for providing cooled air thereto of claim 6, wherein the means for providing a controlled amount of cool air to the envelope further comprise a refrigerant compressor having a cooling coil and wherein the fan blows a controlled amount of air over the cooling coil and into a supply network of tubing.

8. A hypothermic envelope and apparatus for providing cooled air thereto for use with a trauma victim comprising:

coextensive top and bottom portions, the top portion and the bottom portion being sealingly connectable at their peripheries and forming an envelope therebetween;

a means for providing a controlled amount of cool air to the envelope; and wherein the bottom portion further comprises a pouch fixedly attached to a bottom portion bottom edge, the pouch further comprising a closable opening and a means for extending the length of the envelope.

9. The hypothermic envelope and apparatus for providing cooled air thereto of claim 8, wherein the means for extending the length of the envelope further comprise an enclosure having a first edge fixedly attachable to the bottom portion bottom edge and a second edge removably attachable to a top portion bottom edge.

10. The hypothermic envelope and apparatus for providing cooled air thereto of claim 8, wherein the means for providing a controlled amount of cool air to the envelope further comprise a control means for energizing a fan in response to a positive difference between a trauma victim's temperature and a target temperature.

11. The hypothermic envelope and apparatus for providing cooled air thereto of claim 10, wherein the means for providing a controlled amount of cool air to the envelope further comprise a refrigerant compressor having a cooling coil and wherein the fan blows a controlled amount of air over the cooling coil and into a supply network of tubing.

12. A hypothermic envelope and apparatus for providing cooled air thereto for use with a trauma victim comprising:

coextensive top and bottom portions, the top portion and the bottom portion being sealingly connectable at their peripheries and forming an envelope therebetween;

a means for providing a controlled amount of cool air to the envelope; and wherein the top portion further comprises a top portion top layer, a top portion middle layer and a top portion bottom layer, the top portion middle layer further comprising a plurality of spaced-apart conically shaped top portion protrusions and wherein the bottom portion further comprises a bottom portion top layer, a bottom portion middle layer and a bottom portion bottom layer, the bottom portion middle layer further comprising a plurality of spaced-apart conically shaped bottom portion protrusions.

13. The hypothermic envelope and apparatus for providing cooled air thereto of claim 12, wherein the bottom portion middle layer is adapted to support the weight of the trauma victim.

14. The hypothermic envelope and apparatus for providing cooled air thereto of claim 12, wherein the top portion bottom layer and the bottom portion top layer are formed of aluminumized polyethylene.

15. The hypothermic envelope and apparatus for providing cooled air thereto of claim 12, wherein the means for providing a controlled amount of cool air to the envelope further comprise a supply network of tubing having a plurality of supply apertures formed therein fixedly disposed adjacent the bottom portion top layer and a return network of tubing having a plurality of return apertures formed therein fixedly disposed adjacent the top portion bottom layer.

16. The hypothermic envelope and apparatus for providing cooled air thereto of claim 15, wherein the supply network of tubing is fixedly disposed along a plane formed by the area between the plurality of spaced-apart conically shaped bottom portion protrusions.

17. The hypothermic envelope and apparatus for providing cooled air thereto of claim 15, wherein the return network of tubing is fixedly disposed along a plane formed by the area between the plurality of spaced-apart conically shaped top portion protrusions.

18. A hypothermic envelope and apparatus for providing cooled air thereto for use with a trauma victim comprising:

coextensive top and bottom portions, the top portion and the bottom portion being sealingly connectable at their peripheries and forming an envelope therebetween;

a means for providing a controlled amount of cool air to the envelope; and a head area support apparatus comprising three disengagably interlocking splines.

19. The hypothermic envelope and apparatus for providing cooled air thereto of claim 18, wherein the means for providing a controlled amount of cool air to the envelope further comprise a control means for energizing a fan in response to a positive difference between a trauma victim's temperature and a target temperature.

20. The hypothermic envelope and apparatus for providing cooled air thereto of claim 19, wherein the means for providing a controlled amount of cool air to the envelope further comprise a refrigerant compressor having a cooling coil and wherein the fan blows a controlled amount of air over the cooling coil and into a supply network of tubing.

* * * * *